United States Patent
Tanahashi

(10) Patent No.: US 6,497,868 B1
(45) Date of Patent: Dec. 24, 2002

(54) GRAFT POLYMER AND MOULDED MEDICAL ARTICLES EMPLOYING THIS

(75) Inventor: Kazuhiro Tanahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/343,401

(22) Filed: Jun. 30, 1999

Related U.S. Application Data

(63) Continuation of application No. PCT/JP97/04005, filed on Nov. 4, 1997.
(51) Int. Cl.$^7$ .......................... C08F 289/00; A61K 2/16
(52) U.S. Cl. ................. 424/78.08; 424/78.26; 424/78.27; 424/78.31; 424/78.35; 424/78.37; 525/63; 525/66; 525/293; 525/296
(58) Field of Search .......................... 424/78.08, 78.26, 424/78.27, 78.31, 78.35, 78.37; 525/63, 66, 70, 293, 296

(56) References Cited

U.S. PATENT DOCUMENTS

| | | | |
|---|---|---|---|
| 3,844,989 A | * 10/1974 | Kamakura et al. | |
| 5,037,930 A | 8/1991 | Shih | |
| 5,230,711 A | 7/1993 | Keil et al. | |
| 5,254,249 A | * 10/1993 | Terada et al. | 422/44 |
| 5,571,651 A | * 11/1996 | Inaba et al. | 430/109 |

FOREIGN PATENT DOCUMENTS

| | | | |
|---|---|---|---|
| AU | 47581/93 | * | 3/1994 |
| EP | 0 478 445 A1 | | 4/1992 |
| EP | 0 558 357 A1 | | 9/1993 |
| JP | 54-17797 B2 | | 7/1979 |
| JP | 54-18317 | | 7/1979 |
| JP | 64-18317 B2 | | 7/1979 |
| JP | 57-14358 | | 1/1982 |
| JP | 5-140879 A | | 6/1993 |
| JP | 6-256424 A | | 9/1994 |
| JP | 6-337378 A | | 12/1994 |

OTHER PUBLICATIONS

Masao Senuma, et al., "Synthesis and Antibacterial Activity of Copolymers Having a Quaternary Ammonium Salt Side Group" J. Appl. Polym. Sci., 37(10), 1989, pp. 2837–43.
Masao Senuma, et al., "Antibacterial activity of copolymers of trialkyl (4–vinylbenzyl) ammonium chlorides with acrylonitrile", Die Angewandte Makromolekulare Chemie, 204, 1993, pp. 119–25.
Tomiki Ikeda, et al., "Biologically Active Polycations: Antimicrobial Activities of Poly(trialkyl (vinylbenzyl) ammonium chloride)—Type polycations", Macromolecular Chemistry, Rapid Communications, 4(7), 1983, pp. 459–61.

* cited by examiner

Primary Examiner—Jeffrey Mullis
(74) Attorney, Agent, or Firm—Nixon & Vanderhye P.C.

(57) ABSTRACT

The present invention relates to graft polymer which is characterized in that it is formed by graft polymerization of structural units containing. a quaternary ammonium group represented by general formula (A),

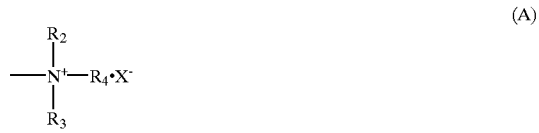

($R_2$ and $R_3$ each represent an alkyl group with from 1 to 3 carbons, and $R_4$ represents an alkyl group with from 3 to 18 carbons. X represents at least one type of ion selected from halogen, sulphate, hydroxide and carboxylic acid ions.), preferably to graft polymer where the structural units containing a quaternary ammonium group represented by general formula (A) are structural units which are represented by general formula (I),

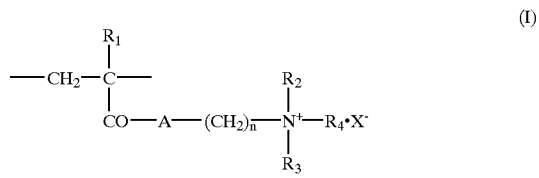

($R_1$ represents at least one species selected from hydrogen, the methyl group and the ethyl group, and n represents an integer in the range 1 to 12. A represents at least one species selected from O, S and $NR_5$. $R_5$ represents hydrogen or an alkyl group with 1 to 12 carbons.) or graft polymer formed by the graft polymerization of structural units containing a quaternary ammonium group and structural units containing an alkoxypolyalkylene glycol moiety represented by the general formula (B),

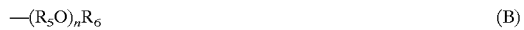

(n represents an integer in the range 1 to 100. $R_5$ represents a straight-chain or branched alkylene group with from 1 to 4 carbons, and $R_6$ represents at least one species selected from hydrogen and straight-chain or branched alkyl groups with from 1 to 4 carbons.).

By applying or incorporating the graft polymer to/in medical devices which are left in the body for a long period, it is possible to prevent microbial infection arising via these medical devices.

9 Claims, No Drawings

GRAFT POLYMER AND MOULDED MEDICAL ARTICLES EMPLOYING THIS

This is a continuation of PCT application PCT/JP97/04005, filed Nov. 4, 1997.

TECHNICAL FIELD

The present invention relates to graft polymer which can be applied to a polymer base material, and to moulded medical articles employing this graft polymer.

TECHNICAL BACKGROUND

In the medical treatment field, infections which occur during the insertion/retention in the patient's body of a medical device comprising a polymer material such as polyurethane constitute a complication and are regarded as a problem. Hitherto, in order to prevent infections accompanying the retention of a medical device, the medical device has either been disinfected just prior to use by immersion, or the like, in an aqueous solution containing an antimicrobial agent or disinfectant such as chlorhexidine or povidone-iodine, or frequent replacement has been carried out in the case of a medical device which can be replaced during treatment. However, because antimicrobial agents and disinfectants disappear from a medical devices surface with time, the disinfection effect does not persist and it is found that when a medical device is used over a long time, this effect gradually declines. Moreover, the frequent replacement of medical devices is a considerable burden to medical workers. Hence, as a further means for preventing infections, medical devices have been subjected to various antimicrobial treatments. Typical thereof are catheters coated on their surface with a layer containing an antimicrobial agent such as dhlorhexidine, or a. metal such as silver or copper or compound thereof. In the case of these catheters, a system is employed for slow release into the body of uniform quantities of the material with an antimicrobial action, and they show a good effect compared to the case where the catheter is disinfected just prior to use.

However, with a system of slow release of an antimicrobial agent, the period of use still has limits and a gradual decline in efficacy is unavoidable. Moreover, the metabolism following slow release of a metal such as silver or compound thereof is unclear, and injury to the body is conceivable. Again, where silver remains in the discarded medical device following use, recovery thereof or other special treatment is required at the time of disposal.

Hence, polymers with quaternary ammonium groups have been variously proposed as polymers which are not of the slow-release type but which have inherent antimicrobial character (Japanese Examined Patent Publication Nos 54-17797 and 54-18817). However, the processability of these polymers is poor, and they cannot alone be formed into moulded articles, so it is necessary either to coat them onto the surface of a moulded polymer which has excellent mechanical characteristics, or to carry out blending and moulding along with such a polymer. However, the better the mechanical characteristics of the base material polymer, the worse its compatibility with other polymers and, where compatibility is poor, a coated polymer peels away or cracks are produced. Now, there has been described in Japanese Unexamined Patent (Kokai) Publication No. 6-337378 a hydrogel containing a copolymer of hydroxypolyalkyleneglycol (meth)acrylate and monomer with a quaternary ammonium salt in a side chain, and again in Japanese Unexamined Patent Publication No. 6-256424 there is described a hydrogel containing a copolymer of a monomer possessing hydroxypolyalkyleneglycol, a monomer possessing a quaternary ammonium salt in a side chain and vinyl monomer. However, in neither case are graft copolymers described and, with these polymers, there are limits to the selective manifestation of the properties of the trunk and graft components. In other words, at present, no antimicrobial polymers are known with satisfactory compatibility to the base material polymer.

The present inventors have considered the problems of the prior-art and, as a result of extensive investigation to obtain an antimicrobial polymer which forms flexible films, such that it can be applied to medical devices of complex shape, and which also has good compatibility and adhesion to various polymers, they have discovered that polymer comprising moieties containing general formula (I) graft polymerized to polymer containing vinyl chloride has good compatibility and adhesion to various polymers and also has a strong antimicrobial action. It is on this discovery that the present invention is based. Thus, the present invention has the objective of offering polymer which can form flexible films and can be suitably applied to base materials of complex shapes; together with moulded medical articles employing this polymer.

DISCLOSURE OF THE INVENTION

The present invention relates to graft polymer which is formed by graft polymerization of structural units containing a quaternary ammonium group represented by general formula (A)

(A)

($R_2$ and $R_3$ each represent an alkyl group with from 1 to 3 carbons, and $R_4$ represents an alkyl group with from 3 to 18 carbons. X represents at least one type of ion selected from halogen, sulphate, hydroxide and carboxylic acid ions.), preferably to graft polymer where the structural units containing a quaternary ammonium group represented by general formula (A) are structural units represented by general formula (I),

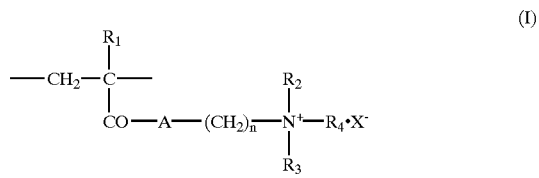

(I)

($R_1$ represents at least one species selected from hydrogen, the methyl group and the ethyl group, and n represents an integer in the range 1 to 12. A represents at least one species selected. from O, S and $NR_5$. $R_5$ represents hydrogen or an alkyl group with from 1 to 12 carbons.), or to graft polymer formed by the graft polymerization of structural units containing a quaternary ammonium group and structural units containing an alkoxypolyalkylene glycol moiety represented by the general formula (B),

(B)

(n represents an integer in the range 1 to 100. $R_5$ represents a straight-chain or branched alkylene group with from 1 to 4 carbons, and $R_6$ represents at least one species selected from hydrogen and straight-chain or branched alkyl groups with from 1 to 4 carbons.).

Furthermore, the present invention relates to moulded medical articles formed by coating aforesaid graft polymer onto a moulded medical article used for insertion into the body, or by blending the graft polymer therewith.

OPTIMUM MODE FOR PRACTISING THE INVENTION

Next, the present invention is explained in further detail.

The graft polymer in the present invention has functional groups represented by formula (A), as stated above. As examples of the structural units with a functional group represented by formula (A), there are structural units wherein formula (A) is bonded to the main chain via an ester linkage, amide linkage, ureido linkage, ether linkage, alkylene group or phenylene group. Of these, from the point of view of ready availability of the precursor, it is preferred that the structural units with a functional group represented by formula (A) are structural units represented by the following formula (I).

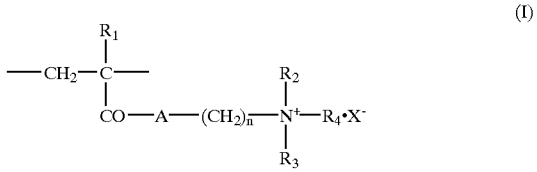

(I)

($R_1$ represents at least one species selected from hydrogen, the methyl group and the ethyl group, $R_2$ and $R_3$ each represent an alkyl group with from 1 to 3 carbons, and $R_4$ represents an alkyl group with from 3 to 18 carbons. n represents an integer in the range 1 to 12. A represents at least one species selected from O, S and $NR_5$. $R_5$ represents hydrogen or an alkyl group with 1 to 12 carbons. X represents at least one ion selected from halogen, sulphate, hydroxide and carboxylic acid ions.)

n represents an integer in the range 1 to 12, but it contributes to the degree of freedom of the antimicrobial functional group and if it is too short then the functional group does not move freely so, for example, it does not readily come into contact with bacteria, while if it is too long then the hydrophobic character is strengthened so that in an aqueous medium containing bacteria the antimicrobial functional group does not readily come into contact with the bacteria.

$R_2$ and $R_3$ are alkyl groups. As the number of carbons is increased, they become more strongly hydrophobic so contact between the antimicrobial functional group and bacteria becomes more difficult. Hence, the number of carbons is from 1 to 3, with the methyl group, which has the least number of carbons, being preferred.

$R_4$ is an alkyl group with from 3 to 18 carbons, preferably with from 8 to 12 carbons. If the alkyl group is branched then movement is restricted, so it is preferred that it be a straight chain.

In the case where X is a sulphate ion, the sulphate ion is normally bivalent but, in the present invention, a monovalent ion may also be coordinated.

Furthermore, A represents at least one species selected from O, S and $NR_5$.

As examples of the precursor vinyl compound used for the graft copolymerization of structural units containing a quaternary ammonium group represented by general formula (A), there are dimethylaminoethyl methacrylate, dimethylaminoethyl acrylate, diethylaminopropyl methacrylate, dimethylaminoethyl acrylamide and diethylaminoethyl acrylamide, but on account of its ready availability the use of dimethylaminoethyl methacrylate is preferred. If the amount of functional groups in the graft polymer is too great, then the coating properties are adversely affected, and again there is a tendency for the compatibility to be lowered when trying to blend with other polymer. On the other hand, if the amount is too small, there is a tendency for the antimicrobial performance to be lowered. Consequently, it is preferred that, in the graft polymer, there be contained a proportion of at least 0.1 mmol but no more than 4 mmol, and preferably at least 0.5 mmol but no more than 4 mmol of the structural units containing an quaternary ammonium group represented by general formula (A) per 1 g of the graft polymer.

In the present invention, there are no particular restrictions on the grafted components other than that containing general formula (A), but there is preferably used a hydrophilic component to enhance the affinity of the material in terms of aqueous solutions and body fluids, etc. For example, there can be used a hydrophilic component containing structural units which include an alkoxypolyalkyleneglycol moiety represented by general formula (B), such as methoxypolyethyleneglycol, ethoxypolyethyleneglycol, methoxypolypropyleneglycol, ethoxypolypropyleneglycol or the like.

(B)

(n represents an integer in the range 1 to 100. $R_5$ represents a straight-chain or branched alkylene group with from 1 to 4 carbons, and $R_6$ represents at least one species selected from hydrogen and straight-chain or branched alkyl groups with from 1 to 4 carbons.).

Of these, the moiety represented by the following general formula (II) is preferred in terms of ready availability and safety.

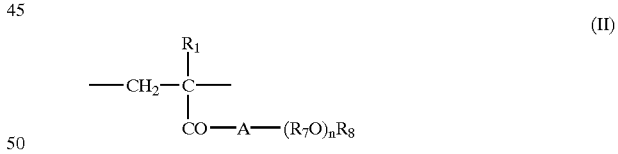

(II)

(Here, $R_1$ represents hydrogen or a methyl group, and n represents an integer from 1 to 100. $R_7$ represents a straight chain or branched alkylene group with from 1 to 4 carbons, and $R_8$ represents at least one species selected from H and straight chain or branched alkyl groups with from 1 to 4 carbons. A represents at least one species selected from O, S and $NR_9$ [where $R_9$ represents hydrogen or an alkyl group with from 1 to 12 carbons].)

As specific examples of the vinyl compounds which are the precursors prior to graft copolymerization, there are methoxypolyethyleneglycol methacrylate, methoxypolyethyleneglycol acrylate and polyethylene glycol methacrylate. If the amount of the hydrophilic component in the graft polymer is too great, then the coating properties are adversely affected, or again the compatibility tends to be lowered when attempting to blend with other polymer.

On the other hand, if there is too little, then there is poor affinity with body fluids and the like, and the biocompatibility is lowered. Consequently, it is preferred that, in the graft polymer, there be contained a proportion of at least 0.01 mmol but no more than 5 mmol, and more preferably at least 0.1 mmol but no more than 1 mmol of structural units containing an alkoxypolyalkyleneglycol represented by general formula (B) per 1 g of the graft polymer.

There are no particular restrictions of the trunk polymer from which the graft copolymer is composed in the present invention, but one containing halogen atoms and in particular chlorine atoms in side chains is preferred. Specifically, there is preferably used polymer containing vinyl chloride. As well as polyvinyl chloride, there can be used various copolymers and blends, such as the copolymers of vinyl chloride and vinyl acetate, which may also include a third component, such as the copolymers with an acrylate, methacrylate, vinyl alcohol, styrene or acrylonitrile, or polymer in which vinyl chloride has been grafted to an ethylene-vinyl acetate copolymer, or blends of these polymers, or mixtures of such polymers with plasticizers, stabilizers and the like. Where blending is carried out, the blending of, for example, polyurethane, natural rubber, silicone resin, polyvinyl chloride, polyamide or synthetic rubber, is preferably employed for moulded medical articles. In these copolymers and blends, the vinyl chloride content should lie in the range from 0.1 to 100%, and can be suitably selected according to the objectives.

The molecular weight of the graft polymer of the present invention is not particularly restricted, but in terms of its number average molecular weight it will be at least about 3,000, preferably from 5,000 to 1,000,000, and more preferably from 30,000 to 100,000 approximately.

Any method may be used for producing the graft polymer of the present invention, but the following example is provided for explanation.

Graft copolymer is obtained by subjecting the polymer which forms the main chains to a graft activating treatment, after which the precursor vinyl compound for the structural units containing formula (A) is added and polymerization carried out by a suitable method.

As the graft activating treatment method, there is preferably used for example the method of replacing chlorine atoms in a polymer containing vinyl chloride by dithiocarbamate groups which readily produce radicals by light irradiation or the like.

In order to obtain quaternary ammonium groups, conversion to the quaternary ammonium salt may be performed with an alkyl halide following graft polymerization using the precursor vinyl compound for the structural units containing general formula (A), but the graft polymerization may also be carried out using precursor vinyl compound which has already be converted into the quaternary ammonium form with an alkyl halide.

The graft polymer of the present invention is preferably used as a medical resin and, in particular, on account of its outstanding antimicrobial properties, it is preferably employed as an antimicrobial resin.

By surface coating, the graft polymer can be applied to any medical device where the prevention of microbial infection is required. Amongst medical devices, where application is made to moulded medical articles inserted into the body, this is particularly effective. Polyurethane, natural rubber, silicone resin, polyvinyl chloride, polyamide, synthetic rubber and the like are preferably used as the material for the medical article inserted in the body.

Amongst moulded medical articles for insertion in the body, the graft polymer can be applied effectively for example to those left for a long period in the body such as catheters, stents, tubes (drainage tubes), cuffs, connectors (tube connectors), access ports, endoscope covers, drainage bags, blood circuits and the like. This because, in contrast to slow release system materials, the antimicrobial functional groups are fixed by covalent bonding to the graft copolymer, and so are safe to the body and their effect persists.

Again, moulded medical articles comprising a blend of the graft polymer of the present invention and an aforesaid polyurethane, natural rubber, silicone resin or the like, can also be effectively used in the same kinds of applications as the aforesaid catheters, stents, tubes and the like.

Below, the present invention is explained in still more specific terms by means of examples, but the present invention is not to be restricted to these examples.

EXAMPLE 1

120 g of polyvinyl chloride of degree of polymerization 550 was dissolved in 2 litres of dimethylformamide, then 2.704 g of sodium diethyldithiocarbamate was added and reaction carried out for 3 hours at 50° C. After reprecipitation in methanol, drying was carried out and there was obtained photo-induced graft activated polyvinyl chloride (hereinafter referred to as DTC-modified polyvinyl chloride).

80 g of this DTC-modified polyvinyl chloride was dissolved in 1250 ml of tetrahydrofuran, then 200 g of methoxypolyethyleneglycol methacrylate (degree of polymerization of the polyethylene glycol portion 20-23) and 80 g of dimethylaminoethyl methacrylate were added, and photo-induced graft polymerization carried out by irradiating for 9.5 hours at 30° C. with a 100 W high pressure mercury lamp (Ushio Denki UM-102) in a photo-reaction device with an interior permeating light source. The composition of the graft copolymer, by weight ratio, was 54% vinyl chloride, 30% methoxypolyethyleneglycol methacrylate and 16% dimethylaminoethyl methacrylate.

EXAMPLE 2

5 g of the graft copolymer described in Example 1 was dissolved in 50 ml of tetrahydrofuran, after which 1.1 ml of butyl bromide was added and reaction carried out for 4 hours at 50° C. After precipitation by pouring into saturated saline, washing was carried out with water and ethanol, followed by drying, and there was obtained an antimicrobial material with quaternary ammonium groups containing a long chain alkyl group (number of carbons=4). The amount of quaternary ammonium groups introduced was 0.15 mmol per 1 g of graft copolymer.

EXAMPLE 3

A polyurethane tube was immersed in its axial direction in a 10% solution of the antimicrobial material described in Example 2, so that the antimicrobial material was applied to the tube, after which it was dried. The tube onto which the material had been applied was then disinfected with alcohol, after which it was immersed in physiological saline in which E. coli (MC106 strain) had been suspended at a concentration of 10 per ml, and the tube left therein for 24 hours. After 24 hours, the number of bacteria adhering to the tube was measured. As a control, the same procedure was followed with a polyurethane tube which had not been coated with the antimicrobial material. As a result, the number of adhering bacteria was 534 in the case of the polyurethane tube to which no antimicrobial material had been applied and 137 in the case of the tube where the antimicrobial material had been applied.

EXAMPLE 4

5 g of the graft copolymer described in Example 1 was dissolved in 50 ml of tetrahydrofuran, after which 1.4 ml of hexyl bromide was added and reaction carried out for 4 hours at 50° C. After precipitation by pouring into saturated saline, washing with water and with ethanol was carried out, followed by drying, and an antimicrobial material with quaternary ammonium groups which contained a long chain alkyl group (number of carbons=6) was obtained. The amount of quaternary ammonium groups introduced was 0.11 mmol per 1 g of graft copolymer.

EXAMPLE 5

A polyurethane tube was immersed in its axial direction in a 10% solution of the antimicrobial material described in Example 4, so that the antimicrobial material was applied to the tube, after which it was dried. As a result of testing in the same way as in Example 3, the number of adhering bacteria was 534 in the case of the polyurethane tube to which no antimicrobial material had been applied and 125 in the case of the tube where the antimicrobial material had been applied.

EXAMPLE 6

5 g of the graft copolymer described in Example 1 was dissolved in 50 ml of tetrahydrofuran, after which 1.7 ml of octyl bromide was added and reaction carried out for 4 hours at 50° C. After precipitation by pouring into saturated saline, washing with water and with ethanol was carried out, followed by drying, and an antimicrobial material with quaternary ammonium groups which contained a l ong chain alkyl group (number of carbons=8) was obtained. The amount of quaternary ammonium groups introduced was 0.30 mmol per 1 g of graft copolymer.

EXAMPLE 7

A polyurethane tube was immersed in its axial direction in a 10% solution of the antimicrobial material described in Example 6, so that the antimicrobial material was applied to the tube, after which it was dried. As a result of testing in the same way as in Example 3, the number of adhering bacteria was 534 in the case of the polyurethane tube to which no antimicrobial material had been applied and 126 in the case of the tube where the antimicrobial material had been applied.

EXAMPLE 8

5 g of the graft copolymer described in Example 1 was dissolved in 50 ml of tetrahydrofuran, after which 2.1 ml of decyl bromide was added and reaction carried out for 4 hours at 50° C. After precipitation by pouring into saturated saline, washing with water and with ethanol was carried out, followed by drying, and an antimicrobial material with quaternary ammonium groups which contained a long chain alkyl group (number of carbons=10) was obtained. The amount of quaternary ammonium groups introduced was 0.16 mmol per 1 g of graft copolymer.

EXAMPLE 9

A polyurethane tube was immersed in its axial direction in a 10% solution of the antimicrobial material described in Example 8, so that the antimicrobial material was applied to the tube, after which it was dried. As a result of testing in the same way as in Example 3, the number of adhering bacteria was 534 in the case of the polyurethane tube to which no antimicrobial material had been applied and 71 in the case of the tube where the antimicrobial material had been applied.

EXAMPLE 10

5 g of the graft copolymer described in Example 1 was dissolved in 50 ml of tetrahydrofuran, after which 2.4 ml of lauryl bromide was added and reaction carried out for 4 hours at 50° C. After precipitation by pouring into saturated saline, washing with water and with ethanol was carried out, followed by drying, and an antimicrobial material with quaternary ammonium groups which contained a long chain alkyl group (number of carbons=12) was obtained. The amount of quaternary ammonium groups introduced was 0.18 mmol per 1 g of graft copolymer.

EXAMPLE 11

A polyurethane tube was immersed in its axial direction in a 10% solution of the antimicrobial material described in Example 10, so that the antimicrobial material was applied to the tube, after which it was dried. As a result of testing in the same way as in Example 2, the number of adhering bacteria was 534 in the case of the polyurethane tube to which no antimicrobial material had been applied and 38 in the case of the tube where the antimicrobial material had been applied.

EXAMPLE 12

5 g of the graft copolymer described in Example 1 was dissolved in 50 ml of tetrahydrofuran, after which 2.7 ml of myristyl bromide was added and reaction carried out for 4 hours at 50° C. After precipitation by pouring into saturated saline, washing with water and with ethanol was carried out, followed by drying, and an antimicrobial material with quaternary ammonium groups which contained a long chain alkyl group (number of carbons=14) was obtained. The amount of quaternary ammonium groups introduced was 0.19 mmol per 1 g of graft copolymer.

EXAMPLE 13

A polyurethane tube was immersed in its axial direction in a 10% solution of the antimicrobial material described in Example 12, so that the antimicrobial material was applied to the tube, after which it was dried. As a result of testing in the same way as in Example 3, the number of adhering bacteria was 534 in the case of the polyurethane tube to which no antimicrobial material had been applied and 151 in the case of the tube where the antimicrobial material had been applied.

EXAMPLE 14

5 g of the graft copolymer described in Example 1 was dissolved in 50 ml of tetrahydrofuran, after which 3.3 ml of octadecyl bromide was added and reaction carried out for 4 hours at 50° C. After precipitation by pouring into saturated saline, washing with water and with ethanol was carried out, followed by drying, and an antimicrobial material with quaternary ammonium groups which contained a long chain alkyl group (number of carbons=18) was obtained. The amount of quaternary ammonium groups introduced was 0.24 mmol per 1 g of graft copolymer.

EXAMPLE 15

A polyurethane tube was immersed in its axial direction in a 10% solution of the antimicrobial material described in Example 14, so that the antimicrobial material was applied to the tube, after which it was dried. As a result of testing in the same way as in Example 3, the number of adhering bacteria was 534 in the case of the polyurethane tube to which no antimicrobial material had been applied and 211 in the case of the tube where the antimicrobial material had been applied.

EXAMPLE 16

By adding dropwise a 1% solution of the antimicrobial material described in Example 10 onto a cover glass, there was applied antimicrobial material to said cover glass, or similarly polyvinyl chloride or polyurethane were applied, and then drying carried out. The cover glass was placed with the side on which the material had been coated upwards, and then on this was added dropwise serum or urine containing $10^3$ to $10^4$ of E. coli, P. aeruginosa, S. aureus, S. epidermidis or E. faecalis, per ml. From above, another cover glass was then placed thereon, sandwiching the bacterial liquid with the side on which the material had been coated at the bottom, after which they were left for 24 hours at 37° C. After washing the cover glasses, they were affixed to an agar medium and the adhering bacteria transferred thereto. After culturing, an assessment was made as to whether or not colonies had formed. As a result it was found that, in the case of a cover glass on which polyvinyl chloride or polyurethane had been applied, colonies of all the bacteria were formed irrespective of whether serum or urine was used, while in the case of the cover glass to which the antimicrobial material had been applied, no colonies were formed of any of the bacteria.

EXAMPLE 17

160 g of the DTC-modified polyvinyl chloride described in Example 1 was dissolved in 2500 ml of tetrahydrofuran, and then 400 g of methoxypolyethyleneglycol methacrylate (average degree of polymerization of the polyethylene glycol portion=90) and 160 g of dimethylaminoethyl methacrylate were added, and photo-induced graft polymerization carried out by 9.5 hours exposure at 30° C. to a 100 W high pressure mercury vapour lamp (Ushio Denki UM-102) in a photo-reaction device with an interior permeating light source. The composition of the graft copolymer, by weight, was vinyl chloride 64%, methoxypolyethyleneglycol methacrylate 21% and dimethylaminoethyl methacrylate 15%.

EXAMPLE 18

30 g of the graft copolymer described in Example 17 was dissolved in 300 ml of dimethylformamide, after which 40 ml of lauryl bromide was added and reaction carried out for 18 hours at 60° C. After precipitating by pouring into a water-methanol mixed solvent, washing and drying were carried out and there was obtained an antimicrobial material with quaternary ammonium groups containing a long chain alkyl group (number of carbons=12). The amount of quaternary ammonium groups introduced was 1 mmol per 1 g of graft copolymer.

EXAMPLE 19

A polyurethane tube was immersed in its axial direction in a 3% solution of the antimicrobial material described in Example 18, so that the antimicrobial material was applied to the tube, after which it was dried. The tube onto which the material had been applied was disinfected with alcohol, after which it was immersed in physiological saline in which S. epidermidis had been suspended at a concentration of $10^4$ per ml, and the tube left therein for 24 hours. After 24 hours, the number of bacteria adhering to the tube was measured. As a control, the same procedure was followed with a polyurethane tube which had not been coated with the antimicrobial material. As a result, the number of adhering bacteria was 967 in the case of the polyurethane tube to which no antimicrobial material had been applied and 0 in the case of the tube where the antimicrobial material had been applied.

EXAMPLE 20

A sheet of styrene-isoprene synthetic rubber was immersed in its lengthwise axial direction into a 3% solution of the antimicrobial material described in Example 17, so that the antimicrobial material was applied to the sheet, after which it was dried. Following drying, it was soaked in water, and even when scratched 20 times with a finger nail, the coating did not peel away.

Industrial Utilization Potential

The graft polymer of the present invention can readily be applied to plastic products, in particular medical devices, and it shows good antimicrobial capacity even when the microbial concentration is high and its effect is maintained over a long period. Moreover, the functional groups which manifest the antimicrobial properties are covalently bonded and are not dissolved away, so the properties are sustained over a prolonged period and the graft polymer is harmless to the body.

What is claimed is:

1. Graft polymer formed by graft polymerization of structural units represented by general formula (A) and structural units represented by general formula (B):

(A)

wherein $R_2$ and $R_3$ each represent an alkyl group with from 1 to 4 carbon atoms, and $R_4$ represents an alkyl group with from 4 to 18 carbons, X represents at least one ion selected from halogen, sulphate, hydroxide and carboxylic acid ions

(B)

wherein n represents an integer in the range 1 to 100, $R_6$ represents a straight-chain or branched alkylene group with from 1 to 4 carbon atoms, and $R_7$ represents at least one member selected from hydrogen and straight-chain or branched alkyl groups with from 1 to 4 carbons wherein the graft polymer contains at least 0.01 mmol of structural units (B) per gram of the graft polymer.

2. The graft polymer according to claim 1 containing at least 0.1 mmol of quaternary ammonium units (A) per gram of graft polymer.

3. The graft polymer according to claim 1 wherein $R_4$ has from 8 to 12 carbons.

4. An antimicrobial resin containing the graft polymer of claim 1.

5. A molded medical article formed by coating or blending the graft polymer of claim 1 onto/with a base material polymer.

6. The molded medical article of claim 5 wherein the base polymer is selected from polyurethane, natural rubber, silicone resin, polyvinyl chloride, polyamide and synthetic rubber.

7. The molded medical articles of claim 6 wherein the base polymer is a polyurethane.

8. A catheter, tube, sheath, stent, cuff, tube connector, access port, drainage bag, endoscope cover or blood circuit according to claim 5.

9. The graft polymer according to claim 1 wherein the structural units (A) are represented by general formula (I):

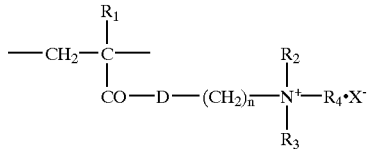

$R_1$ is hydrogen, methyl or ethyl group, and n represents an integer in the range 1 to 12, and D is O, S or $NR_5$, in which $R_5$ is hydrogen or an alkyl group with from 1 to 12 carbons.

* * * * *